(12) United States Patent
Marincek et al.

(10) Patent No.: US 10,277,001 B2
(45) Date of Patent: Apr. 30, 2019

(54) LASER SYSTEM AND METHOD FOR CONTROLLING THE LASER PULSE SHAPE

(71) Applicant: Fotona d.d., Ljubljana (SI)

(72) Inventors: Marko Marincek, Ljubljana (SI); Janko Nendl, Ljubljana (SI); Matjaz Mocnik, Ljubljana (SI); Lukac Matjaz, Ljubljana (SI)

(73) Assignee: Fotona d.d., Ljubljana (SI)

( * ) Notice: Subject to any disclaimer, the term of this patent is extended or adjusted under 35 U.S.C. 154(b) by 751 days.

(21) Appl. No.: 14/938,379

(22) Filed: Nov. 11, 2015

(65) Prior Publication Data

US 2016/0149370 A1 May 26, 2016

(30) Foreign Application Priority Data

Nov. 24, 2014 (EP) .................................... 14194451

(51) Int. Cl.
*A61B 18/20* (2006.01)
*A61N 5/06* (2006.01)
(Continued)

(52) U.S. Cl.
CPC .......... *H01S 3/0912* (2013.01); *A61B 18/203* (2013.01); *A61B 18/245* (2013.01);
(Continued)

(58) Field of Classification Search
CPC ... H01S 3/0912; A61B 18/245; A61B 18/203; A61B 2018/00577; A61B 2018/00476;
(Continued)

(56) References Cited

U.S. PATENT DOCUMENTS

2008/0069172 A1  3/2008  Rizoiu et al.

FOREIGN PATENT DOCUMENTS

WO    98/55035 A1   12/1998
WO    98/57526 A2    3/2008
(Continued)

OTHER PUBLICATIONS

Extended European Search Report for corresponding European Patent Application No. 14194451.2 dated May 12, 2015.

*Primary Examiner* — Boniface Nganga
(74) *Attorney, Agent, or Firm* — Renner, Otto, Boisselle & Sklar, LLP (57) ABSTRACT

A laser system for medical treatment is disclosed which comprises a pump, wherein the laser system is adapted to be operated in pulsed operation so that at least one laser pulse of a temporally limited pulse duration ($T_p$) is generated. The generated laser pulse irradiates some part of the human or animal body so that a two-dimensional laser spot S is located on the top layer of the irradiated part of the human or animal body. The pump power of the pump of the laser system is modulated in such a way that the cumulative energy $E_S(T_p/2)$ which is delivered by said laser pulse to said laser spot S during the first half of the pulse duration is less than 45% of the energy $E_S(T_p)$ which is delivered by said laser pulse to said laser spot S during the entire pulse duration $T_p$.

12 Claims, 7 Drawing Sheets

(51) Int. Cl.
*A61N 5/067* (2006.01)
*H01S 3/091* (2006.01)
*A61B 18/24* (2006.01)
*A61B 17/00* (2006.01)
*A61B 18/00* (2006.01)

(52) U.S. Cl.
CPC ............. *A61B 2017/00159* (2013.01); *A61B 2018/00029* (2013.01); *A61B 2018/00476* (2013.01); *A61B 2018/00577* (2013.01); *A61B 2503/40* (2013.01); *A61N 5/06* (2013.01); *A61N 2005/067* (2013.01)

(58) Field of Classification Search
CPC .. A61B 2018/0029; A61B 2017/00159; A61B 2503/40; A61B 18/20; A61N 2005/067; A61N 5/06
See application file for complete search history.

(56) References Cited

FOREIGN PATENT DOCUMENTS

| | | |
|---|---|---|
| WO | 2010/150175 A1 | 12/2010 |
| WO | 2013/159793 A1 | 10/2013 |

LASER SYSTEM AND METHOD FOR CONTROLLING THE LASER PULSE SHAPE

This application claims priority of European Application No. 14194451.2 filed Nov. 24, 2014, which is hereby incorporated herein by reference.

FIELD OF THE INVENTION

The present invention relates to a laser system and methods for controlling the temporal shape of laser pulses for achieving beneficial effects on treated parts of the human and animal body.

BACKGROUND OF THE INVENTION

Prior Art

Lasers have been used to treat medical conditions for several decades. Because of their properties and the range of wavelengths available, they have been used to treat a variety of indications in surgery, dentistry, dermatology, aesthetics, gynecology, ophthalmology, etc.

In order to limit the undesired heat diffusion into surrounding tissue, pulsed lasers with temporally limited laser pulses are typically used for tissue treatments. When laser pulses of limited duration are used, the energy loss caused by heat diffusion during the pulse is reduced, resulting in higher treatment efficiency and target selectivity. During a lengthy laser exposure, most of the deposited heat will diffuse away from the target structure, resulting in non-specific thermal damage to adjacent tissue. Conversely, an adequately short laser pulse minimizes the time available for heat diffusion and confines the heating effect to the target structure, resulting in maximal temperature differences between the target and adjacent structures. However, even with pulsed lasers, controlling the effects of heat diffusion remains a challenge. The reason for this is that the laser intensity/laser power is usually not constant over the duration of the pulse, but varies—due to different reasons that will be explained below—so that a specific temporal pulse intensity/power profile or temporal pulse shape is formed. Consequently, the tissue effects may vary considerably during a single pulse depending on the temporal pulse shape.

The temporal pulse shape of free-running lasers is predominantly determined by the temporal shape of the pumping power. In free-running lasers, the quality of the laser resonator remains fixed during laser pumping and operation. The pumping means typically comprises at least a pulsed current source. In certain types of lasers, such as diode or gas lasers, the current flows directly from the current source through the laser material (a semiconductor or a gas) within the laser source and pumps the laser source, in order to generate output laser pulses. In yet other laser types such as solid-state lasers, the pumping means additionally comprises an optical pump light source such as a flash lamp or a diode, and the pulsed current from the current source flows through the optical pump light source that pumps the laser source in a pulsed manner, in order to generate output laser pulses.

Figure 6:
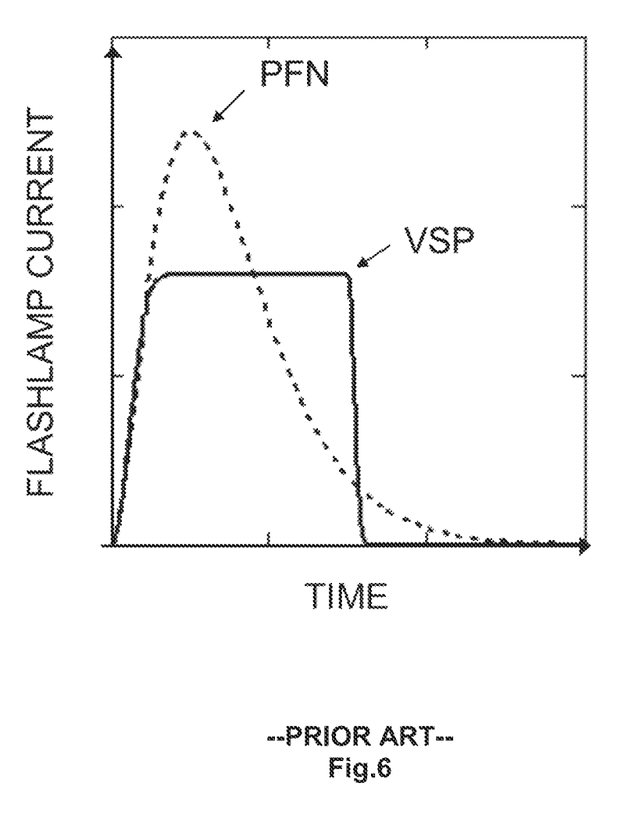
FIG. 6 examples of PFN and VSP flash lamp current pulses.

Flash lamps are commonly used for optically pumping medical lasers used for different tissue treatments. The conventional method of pulsing a flash lamp is to discharge a pulse forming network (PFN) through the flash lamp. A pulse forming network is comprised of a capacitor used to store electrical energy, and an inductance which is used to limit the discharge current into the flash lamp load. An example for the flash lamp current which is generated by the PFN method is shown in FIG. 6 (dashed line).

PFN-generated flash lamp light pulses and the resulting laser output pulses have a typical asymmetrical bell-like temporal pulse shape with a relatively short rise time and a long declining tail. PFN laser pulses are therefore "left-shifted", with the intensity peak located on the time axis closer to the beginning than to the end of the pulse.

Figure 2:
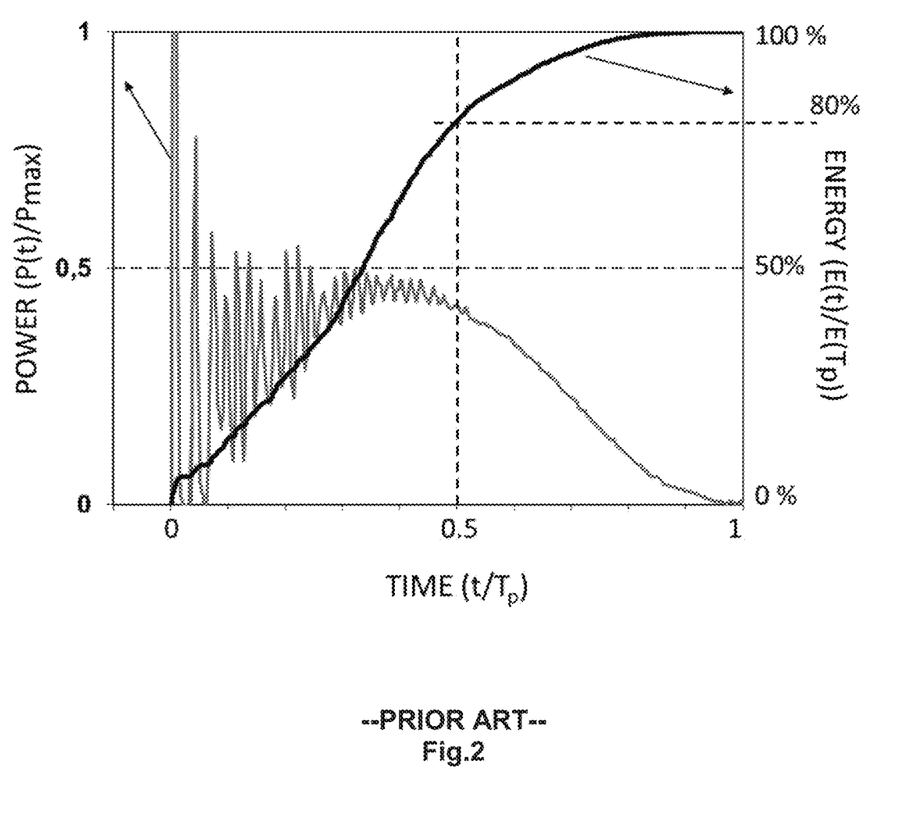
FIG. 2 an example of a measured power (intensity) shape of a prior art PFN laser pulse, together with the corresponding temporal development of the cumulative laser energy.

FIG. 2 depicts a typical example of a prior art PFN laser pulse. As seen from FIG. 2, the laser pulse power (P)/intensity (I) starts to rise relatively sharply until the power maximum ($P_{max}$) is reached at approximately $1/10^{th}$ of the overall pulse duration ($T_p$), followed by a very slow decay tail that lasts for the remaining $9/10^{th}$ of the laser pulse. The duration of the particular measured pulse was approximately $T_p$=600 microseconds.

In some applications, particularly in dentistry, water spray is often used to moisten and cool the tissue surface. For such applications, a prior art apparatus for imparting disruptive forces to the target (EP 1560470) requires that the laser pulse is left-shifted so that the full width half maximum of the laser pulse is located on the time axis closer to the beginning than to the end of the pulse.

Another type of current source for pumping flash lamps of medical lasers according to the prior art is a variable square pulse (VSP) power supply. Here, a fraction of energy stored in a large capacitor bank is discharged through the flash lamp which provides nearly square-shaped flash lamp pump pulses. The solid line in FIG. 6 illustrates an example for the flash lamp current which is generated by the VSP method.

The resulting output laser pulses which are generated by the VSP method do not only have a very short rise time, but as opposed to PFN pulses, also a very short decay time. Nevertheless, VSP pulses still tend to exhibit a left shift so that the full width half maximum (FWHM) of the laser pulse is located on the time axis closer to the beginning than to the end of the pulse, particularly if the pulses are of shorter duration (less than approximately 300 microseconds).

A disadvantage of prior art PFN and VSP pulse shapes is that due to the short flash lamp current ramp-up time, the laser pulse starts with sharp spikes of high intensity/power resulting in very high intensities at the beginning of the pulse, which can be an order of magnitude higher than the average pulse intensity. Further, these initial intensity/power spikes also have a low beam divergence so that these spikes of high intensity are focused to a small region within the overall laser beam spot. As a result of this, at the beginning, the effect of the pulse on tissue effects can be substantially different than the intended effect which takes into account the average pulse intensity/power. In addition, high intensity oscillations at the beginning of the pulse can damage the delivery optics like output windows and fiber tips.

Prior art left-shifted pulses are disadvantageous also from the perspective of their effect on the treated tissue. Since the most intense part of a left-shifted pulse occurs in the early stages of the pulse, the overall laser pulse parameters have to be optimized to obtain a desired treatment effect from this part of the pulse. At the same time, no damage to the tissue should result from the above-described high intensity early stage of the pulse. Therefore, the energy contained in the remaining decay tail of the pulse which has a suboptimal intensity is wasted and may even be harmful to the treated tissue. For example, in certain types of treatments, lasers are used for ablation of hard and soft body tissues such as dental enamel, dentine, bone material, skin and mucosa. The removal of material in tissue ablation is based on a pronounced absorption of the laser light in the ablated tissue.

The absorption of laser light leads to local heating with sudden evaporation that causes material removal. For a left-shifted laser pulse, it holds only during the initial intense part of the pulse that the rate of ablation is faster than the rate at which heat diffuses into the tissue. Therefore, only during the early stage of the pulse, the ablation is energy-efficient and occurs without thermal effects for deeper layers of the tissue. After the maximum laser intensity of a laser pulse is reached, the intensity starts to fall and forms a long pulse tail during which heat diffusion dominates over the ablation rate. As a result, the thermally affected layer of tissue that is not ablated by the end of the laser pulse is relatively thick. For most medical procedures this is not desirable, since it may result in thermal damage and even tissue necrosis.

In addition, when water spray is used to moisten and cool the tissue surface, particularly in dentistry, the most powerful leading part of the pulse is used to evaporate the water droplets and water lines on the tissue surface, leaving the less powerful portion to ablate the tissue. Additionally, the fast water evaporation generated by the intense portion of the pulse results in a large turbulent cloud of water vapor, water droplets and ablation particles (further on referred to as "vapor cloud"), which forms above the surface and absorbs and further scatters the intense portion of the laser pulse. This lowers the efficiency and precision of ablation, reduces speed and causes heating of the tooth.

SUMMARY OF THE INVENTION

The invention has the object to provide an improved laser system and methods for tissue treatment, with an aim to reduce initial high laser intensity spiking and deliver the energy in a temporally beneficially shaped laser pulse such that most of the pulse energy is utilized beneficially for the intended effect on the tissue.

This object is solved by a laser system having the features of claim 1. According to one aspect of the present invention, a laser system is used for medical treatment, wherein the laser comprises a pump, and wherein the laser system is adapted to be operated in pulsed operation so that at least one laser pulse of a temporally limited pulse duration ($T_p$) is generated and said laser pulse irradiates some part of the human or animal body so that a two-dimensional laser spot S is located on the top layer of the irradiated part of the human or animal body. Further, the pump power of the pump is modulated in such a way that the cumulative energy $E_S(T_p/2)$ which is delivered by said laser pulse to said laser spot S during the first half of the pulse duration is less than 45% of the energy $E_S(T_p)$ which is delivered by said laser pulse to said laser spot S during the entire pulse duration. Here, the cumulative energy $E_S(T)$ until time T is defined in eq. (2) below and the pulse duration/pulse width $T_p$ of the laser pulse is defined as the time difference between the start of the laser pulse at t=0 and the time when 99% of the total cumulative energy has been delivered. Further, it should be noted that various definitions are possible for the laser spot size S.

Thus, the laser pulse which is generated by this laser system is right-shifted. As explained above and also further below with respect to specific embodiments, for many medical treatments, it is beneficial that, during the initial pulse development, the laser pulse being used has a rather low intensity/power and, during the final stage, has a significantly higher intensity/power. In particular, these right-shifted laser pulses lead to less thermal damage in deeper layers of the treated tissue and/or the surroundings of the treated tissue.

Preferably, the cumulative energy $E_S(T_p/2)$ which is delivered by said laser pulse to said laser spot S during the first half of the pulse duration is less than 35% of the energy $E_S(T_p)$ which is delivered by said laser pulse to said laser spot S during the entire pulse duration, more preferably the fraction of the cumulative pulse energy during the first half is less than 25% and, most preferably, less than 10%.

According to another aspect of the present invention, the power of the pump is risen sufficiently slowly that, for times T in the interval $[T_p/20, T_p/2]$, it holds for the cumulative pulse energy $E_S(T)$ which is delivered by said laser pulse to said laser spot S until time T $$E_S(T) < 0.5 \cdot T \cdot \frac{E_S(T_p)}{T_p},$$

wherein $E_S(T_p)$ is the energy which is delivered by said laser pulse to said laser spot during the entire pulse duration $T_p$, wherein the laser pulse starts at t=0. Since, according to the definition in eq. (2) below, the cumulative pulse energy is the integral of the pulse power over time, the ratio $E(T_p)/T_p$ which is used in the above inequality can be seen as the average pulse power which is delivered during the entire pulse duration $T_p$. Thus, the above inequality specifies that for times T during the initial phase, the ratio $E(T)/T$ is at least twice smaller than this average pulse power. As a consequence, the pulse intensity/power of the laser pulse is kept at rather low values during the initial phase of the pulse. Keeping the pulse intensity/pulse power low during the initial phase of the pulse is helpful for obtaining a laser pulse which is right-shifted (in the sense as specified above). Moreover, a rather low pulse intensity/pulse power during the initial phase has the additional advantage that the spikes of the laser pulse have a much lower intensity during this initial phase of the laser pulse. Therefore, the above-described disadvantages which result from the initial high intensity spikes of the prior art PFN and VSP laser pulses are avoided. Besides, the preceding low intensity part of a laser pulse beneficially preheats tissue and enhances the treatment effect of the subsequent high intensity part of the pulse.

According to a preferred aspect of the present invention, the laser pulse comprises a plurality of micro-pulses, wherein in between two micro-pulses of the laser pulse there is a temporal region of the pulse where the pulse intensity/pulse power is smaller than $1/10^{th}$ of the maximal pulse intensity in the neighboring two micro-pulses. Preferably, the time duration of such a temporal region with reduced intensity lies between 1 microseconds and 2 milliseconds. The advantage of a pulse which consists of a plurality of micro-pulses is that the treated tissue can cool down during the time span which lies in between two micro-pulses. As a result, the thermal damage to deeper tissues layers and/or the surroundings of the treated tissue is reduced.

A laser system for tissue treatment is proposed, comprising a control unit, a pumping means, a laser source and a delivery system, wherein the laser system is adapted to be operated to generate temporally limited individual output laser pulses with a temporal pulse length ($T_p$) and wherein the pumping pulse is shaped in a way to produce a laser pulse with a smooth pulse initialization, continuing in fast pulse rise and almost immediate pulse drop after the pumping pulse is stopped.

According to the invention, an electronic circuit is used for controlling the temporal characteristics of the pumping current of the flash lamp. This can be done with fast IGBT switching via Pulse Width Modulation (PWM) of the flash lamp current.

BRIEF DESCRIPTION OF THE DRAWINGS

Some of the embodiments of the invention will be explained in the following with the aid of the drawings in more detail. It is shown in.

DETAILED DESCRIPTION

Figure 1:
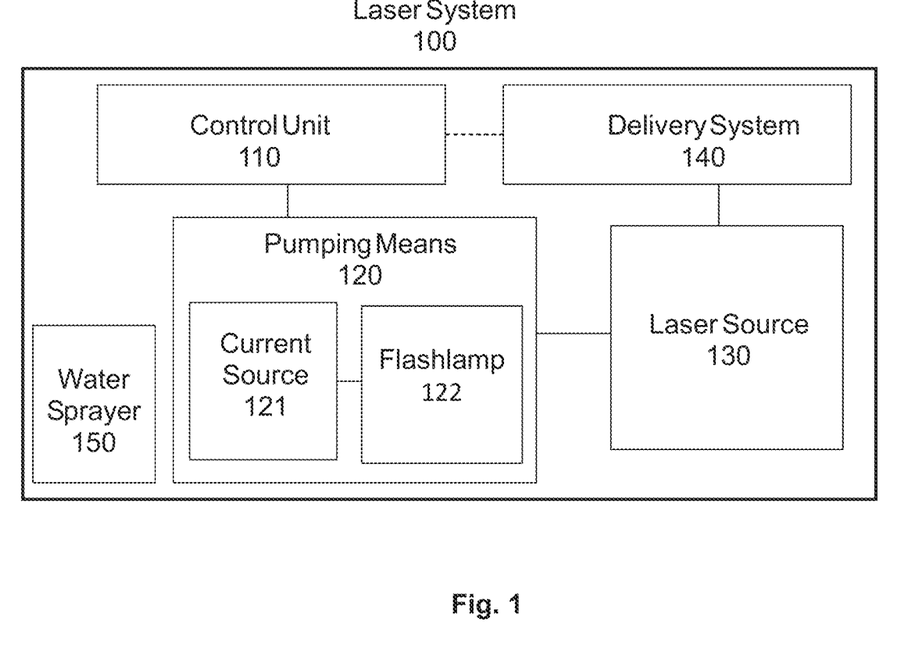
FIG. 1 a scheme of a laser system according to the invention

With reference now to FIG. 1, in various embodiments, a laser system 100 comprises a control unit 110, a pumping means 120, a laser source 130, and a light delivery system 140 wherein the laser system is adapted to be operated to generate temporally limited individual output laser pulses with an overall temporal pulse length $T_p$ and wherein the intensity within the individual pulse does not exhibit high intensity spiking in the early stage of the pulse development. The laser system may be operated such that these modulated individual pulses follow one another at a suitable temporal period ($T_F$).

In some of the preferred embodiments, the laser source 130 operates in a wavelength range from above 1.9 to 11 microns, such as solid-state Tm:YAG laser (wavelength of 2.0 microns), solid-state Ho:YAG laser (wavelength of 2.1 microns), solid-state Er:YAG laser (wavelength of 2.94 microns) and solid-state Er,Cr:YSGG laser (wavelength of 2.79 microns), or gas $CO_2$ laser (wavelength 9.3 to 10.6 microns) that is highly absorbed in water which is the major constituent of organic tissue. However, wavelengths below 1.9 microns may be used as well. Lasers with a wavelength below 1.9 microns may include a solid-state Nd:YAG laser (wavelength of 1.44, 1.32 or 1.06 microns), a solid-state Nd:YAP laser (wavelength of 1.34 or 1.08 microns), a solid-state alexandrite laser (0.755 μm), a solid state ruby laser (0.964 μm), a solid-state KTP:YAG laser (wavelength of 0.53 microns) and various diode lasers (wavelengths in a range from 0.8 to 2.1 microns).

According to the invention, the laser pumping means 120 comprises at least a current source 121 wherein its output current is controlled by the control unit 110 in such a manner to generate temporally limited pulses with a beneficial shape.

In some of the embodiments such as diode lasers or gas lasers, the current from the current source 121 flows directly through the laser material (a semiconductor or a gas) within the laser source 130 and pumps the laser source 130 to generate inventive output laser pulses. In yet other embodiments, the pumping means 120 consists additionally of an optical pump light source 122 such as a flash lamp or a diode, and the current from the current source 121 flows through the optical pump light source 122 that pumps the laser source 130, such as a solid-state laser, to generate inventive output laser pulses.

Flash lamps are commonly used to optically pump medical lasers. The conventional method of pulsing a flash lamp is to discharge a pulse forming network (PFN) through the flash lamp. A pulse forming network is comprised of capacitor to store electrical energy and inductance to limit the discharge current into the flash lamp load. The laser pulses resulting from PFN pumped flash lamp optical pulses are most commonly asymmetricall bell-shaped and of fixed duration $T_p$.

In order to obtain a quantitative measure for the left- or right-shifted shape of a pulse, we consider the situation of interest that the laser pulse is used for a medical treatment. Accordingly, the laser pulse will be directed to the treated part of the human or animal body so that a laser spot is generated which is adjacent to the treated part of the human or animal body.

Turning to the definition of left-shifted and right-shifted laser pulses, we start from the cumulative fluence at a point (x,y) within the laser spot which is given as $$F(T; x, y) = \int_0^T I(t; x, y) dt \qquad \text{Eq. (1)}$$

Here, I(t;x,y) is the pulse intensity at point (x,y) at time t and the pulse starts at t=0.

Here, it should be noted that there are various possible possibilities for defining the laser spot (and the corresponding laser spot size) for a laser beam. For example, one can use the criterion that the intensity should be greater than $1/e^2$ or the FWHM criterion. In some embodiments, it is preferable that the laser spot is a time independent quantity even when the profile of the laser pulse varies over time. A time independent laser spot can be defined by requiring, for example, that only such a point (x, y) belongs to the laser spot for which the cumulative fluence $F(T_p;x,y)$ at this point over the entire pulse duration $T_p$ is greater than $1/e^2$ of the maximum cumulative fluence $F_{max}(T_p)$ of the laser at time $T_p$.

If one integrates Eq. (1) over the laser spot size S, one obtains $$E_S(T) = \int_S F(T; x, y) dx dy = \int_0^T \left[ \int_S I(t; x, y) dx dy \right] dt = \int_0^T P_S(t) dt. \qquad \text{Eq. (2)}$$

Here, $E_S(T)$ is the cumulative energy which is delivered by the laser pulse to the laser spot S from the beginning of the pulse until time T, while $P_S(t)$ is the power of that part of the pulse which lies within the laser spot S at time t.

If one divides Eq. (2) by the area of the laser spot S, one obtains $$F_{av,S}(T) = \int_0^T I_{av,S}(t) dt \qquad \text{Eq. (3)}$$

Here, $F_{av,S}(T)$ is the average fluence within the laser spot S until time T, and $I_{av,S}(t)$ is the average intensity within the laser spot S at time t.

If one uses Eq. (2), a left-shifted pulse is a pulse for which the cumulative energy $E(T_p/2)$ delivered during the first half of the pulse is greater than 50% of the total cumulative energy, i.e. $E(T_p/2) > 0.5\ E(T_p)$. In this context, the beginning of a laser pulse is the time when the pulse power is no longer zero (in the above equations, t=0 at the beginning of the pulse), whereas the pulse duration/pulse width $T_p$ of the laser pulse is defined as the time difference between the beginning of the pulse and the time when 99% of the total cumulative energy has been delivered.

It should be noted that the laser pulse intensity may not have a continuous pulse shape, but may instead consist of a number of intensity spikes or micro-pulses, wherein the pulse intensity may be negligible or even zero in between these spikes or micro-pulses. Further, these micro-pulses can be present during the whole pulse duration or only during certain parts of the pulse. The full width half maximum (FWHM) of the micro-pulses may be from 0.1 microseconds to 2 milliseconds, and the duration of the temporal periods when the intensity is very small or zero may be from 0.1 microseconds to 5 milliseconds. Even though the pulse intensity can drop to the value of zero in between the micro-pulses, these micro-pulses belong to a single laser pulse, since the pulse repetition time ($T_F$) of the laser, i.e., the time between two separate laser pulses is much longer than any time interval in between two micro-pulses. Likewise, the above-mentioned criterion for the end of an individual laser pulse as the time when 99% of the total cumulative energy of the laser pulse has been delivered can be equally applied to laser pulses which consist of micro-pulses.

Here and in the following, we often suppress the dependence on the laser spot S, since, typically, it does not matter for the question whether a pulse is left-shifted or right-shifted which definition of the laser spot is used. A pulse is considered strongly left-shifted when at least 75% of the total energy is delivered during the first half of the pulse. Similarly, a pulse is strongly right-shifted when the cumulative energy delivered during the last half of the pulse represents at least 75% of the total energy.

Using equivalent eq. (3), a left-shifted pulse can be also defined as a pulse for which the cumulative average fluence $F_{av}(T_p/2)$ delivered during the first half of the pulse is greater than 50% of the total cumulative average fluence, i.e. $F_{av}(T_p/2) > 0.5\ F_{av}(T_p)$.

In some embodiments, it is preferable for the definition of left-shifted and right-shifted pulses that one refers to the total power of laser pulse at time t, i.e. one no longer considers only the "localized" pulse power within the laser spot, but considers the pulse power lying in the entire plane that is perpendicular to the direction of propagation of the laser pulse (i.e, in eq. (2) above, pulse intensities and pulse fluences would be integrated over the entire x, y plane).

In these embodiments, the cumulative energy of the laser pulse until time T is defined as $$E(T) = \int_0^T P(t)dt \qquad \text{Eq. (4)}$$

The cumulative energy E(T) grows with time until at $T=T_p$ the total energy of the laser pulse $E_p$ has been delivered. The skewness of a pulse would then be defined by using the quantity E(T) according to Eq. (4), i.e. for a left-shifted laser pulse, $E(T_p/2)$ is greater than $0.5\ E(T_p)$, whereas, for a right-shifted pulse, it is smaller than $0.5\ E(T_p)$.

It should be also noted that the present invention is concerned with medical treatments which use laser pulses which have a significant shift to the right, i.e. the cumulative energy which is delivered during the second half of the pulse duration should be at least 55% of the cumulative energy during the entire pulse duration. Here, the cumulative energy can be either the energy which is delivered to the laser spot (cf. eq. (2) above) or the cumulative energy of the laser pulse itself (cf. eq. (4) above).

For the particular example of a prior art PFN pulse shown in FIG. 2, the cumulative average fluence delivered during the first half of the pulse represents 80% of the total fluence, signifying that the pulse is strongly left-shifted. As explained above, one should also note the high initial intensity spikes exhibited by the prior art PFN pulse shown in FIG. 2.

Another type of pumping current source for a flash lamp according to the prior art is a variable square pulse (VSP) power supply. Here, a fraction of energy stored in a large capacitor bank is discharged through the flash lamp which provides nearly square shaped flash lamp pump pulses that result also in nearly square shaped output laser pulses, the duration of which ($T_p$) can be conveniently controlled over a wide range of pulse duration by opening and closing a switching transistor, for example an IGBT transistor.

Figure 3:
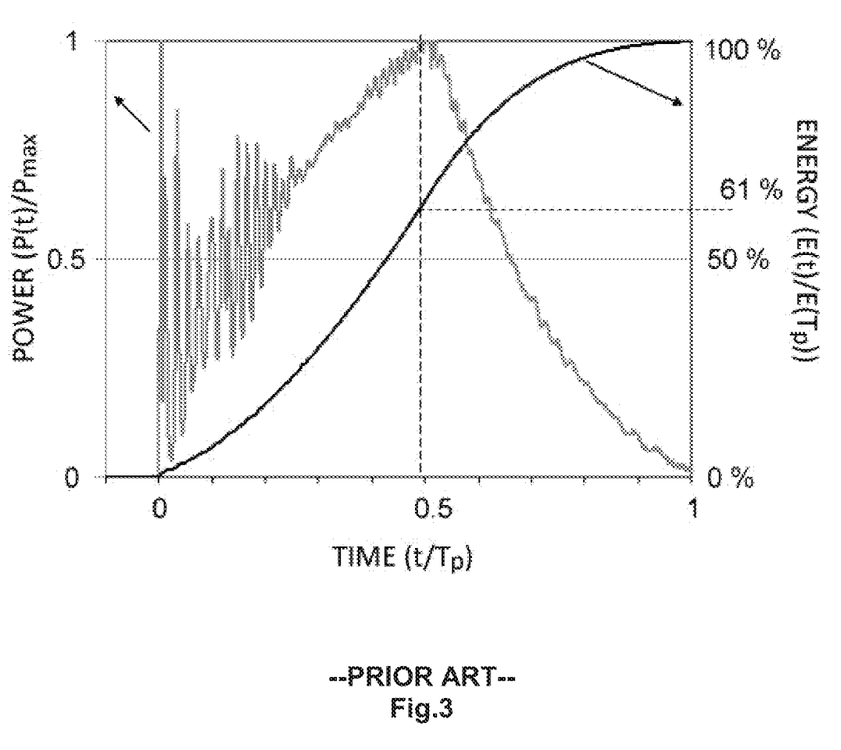
FIG. 3 an example of a measured power (intensity) shape of a prior art VSP laser pulse, together with the corresponding temporal development of the cumulative laser energy.

An example of a prior art VSP pulse is shown in FIG. 3. The depicted pulse shape was obtained by measuring an output from a commercially available flash lamp pumped solid-state Er:YAG dermatological laser (Dynamis XS, manufactured by Fotona). The approximate duration of the particular measured pulse was $T_p$=300 microseconds. As can be seen from FIG. 3, the VSP generated pulse does not have as long a decay tail as is the case with the PFN pulse shown in FIG. 2. The intensity maximum is reached at approximately ½ of the pulse. Nevertheless, the pulse is still left-shifted since approximately 60% of the energy is delivered already within the first half of the pulse.

As in FIG. 2 and explained above, note again the initial high intensity (power) spikes exhibited also by the prior art VSP pulse shown in FIG. 3.

Most commonly used prior art flash lamp pumping current sources for medical lasers (PFN and VSP) are not well suited for creating inventive modulated laser pulses. Instead, in one preferred embodiment, a pulse width modulation (PWM) power supply may be used. The setup for modulating the flash lamp pumping pulse intensity is described as follows. Electrical energy is stored in a large capacitor bank connected to the flash lamp via a fast switching IGBT transistor. The flash lamp is first put into the low current conductive state controlled by a separate simmer power supply. The pumping pulse is initiated by switching the IGBT into the conductive state starting the electrical current to enter the flash lamp from the capacitor bank. By switching the IGBT with a train of control pulses the current through a flash lamp reaches a desired value depending on the electrical characteristics of the electronic circuit, switching frequency and pulse-width of the train of pulses. Preferably, the switching-off time of the IGBT electronic switch is shorter than 50 microseconds in order to obtain sufficiently fast cut-off of the right-shifted pulse.

The effective current through the flash lamp can be thus controlled on-line with a processor by applying the pulse width modulation of the IGBT switching signal.

Figure 4:
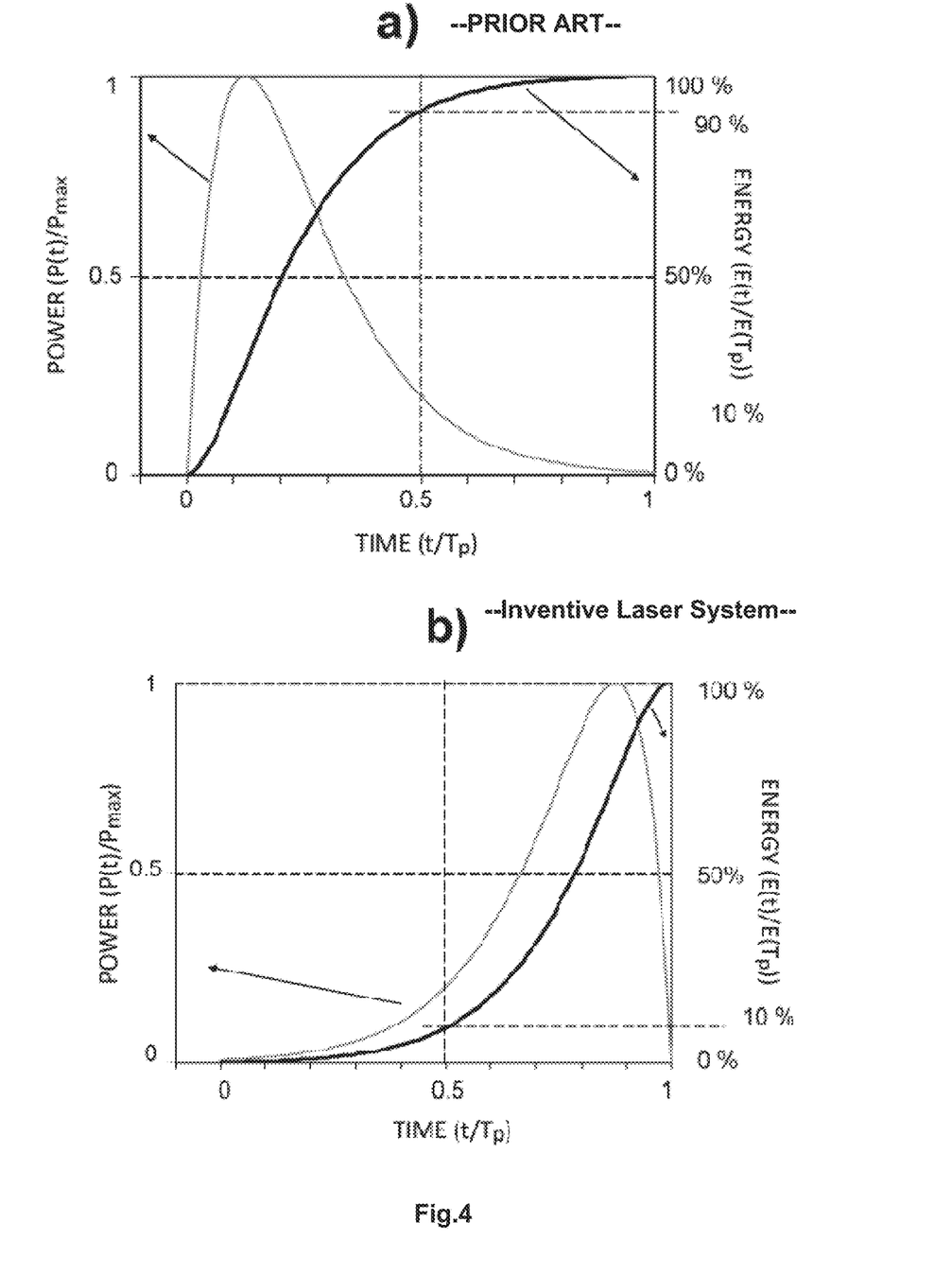
FIG. 4 a schematic illustration of the difference between the temporal developments of the laser intensity in a) a prior art pulse; and in b) an inventive laser pulse.
Figure 5:
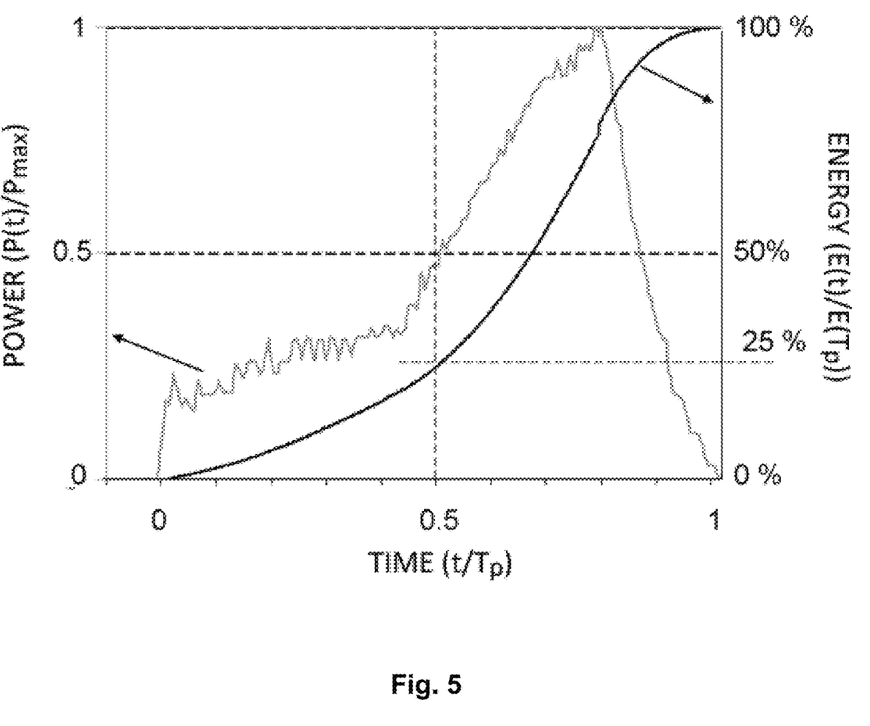
FIG. 5 an example for the temporal development of the power/intensity in a PWM laser pulse according to the present invention.

FIG. 4 shows a schematic example of a prior art pulse from a medical laser (FIG. 4a), together with a schematic example of an embodiment of an inventive laser pulse for tissue treatment (FIG. 4b). The depicted prior art pulse starts quickly until it reaches its maximum amplitude ($I_{max}$), and ends with a long decay tail. According to the definition given above, the prior art pulse (FIG. 4a) is strongly left-shifted, since approximately 90% of the cumulative energy is delivered during the first half of the pulse. On the other hand, the depicted inventive laser pulse (FIG. 4b) starts slowly and ends with a fast growth up to its maximum amplitude, followed by a relatively fast decline to the zero value. The depicted inventive pulse is strongly right-shifted since only approximately 10% of the cumulative energy is delivered during the first half of the pulse. Here, the end of the laser pulse is defined as the time when 99% of the total cumulative energy has been delivered FIG. 5 shows an example of an embodiment of an inventive laser pulse as experimentally obtained by suitably PWM modulating the current through a flash lamp pumped solid-state Er:YAG laser. The obtained pulse shape is strongly right-shifted since only approximately 25% of the total cumulative energy is delivered during the first half of the pulse.

Figure 7:
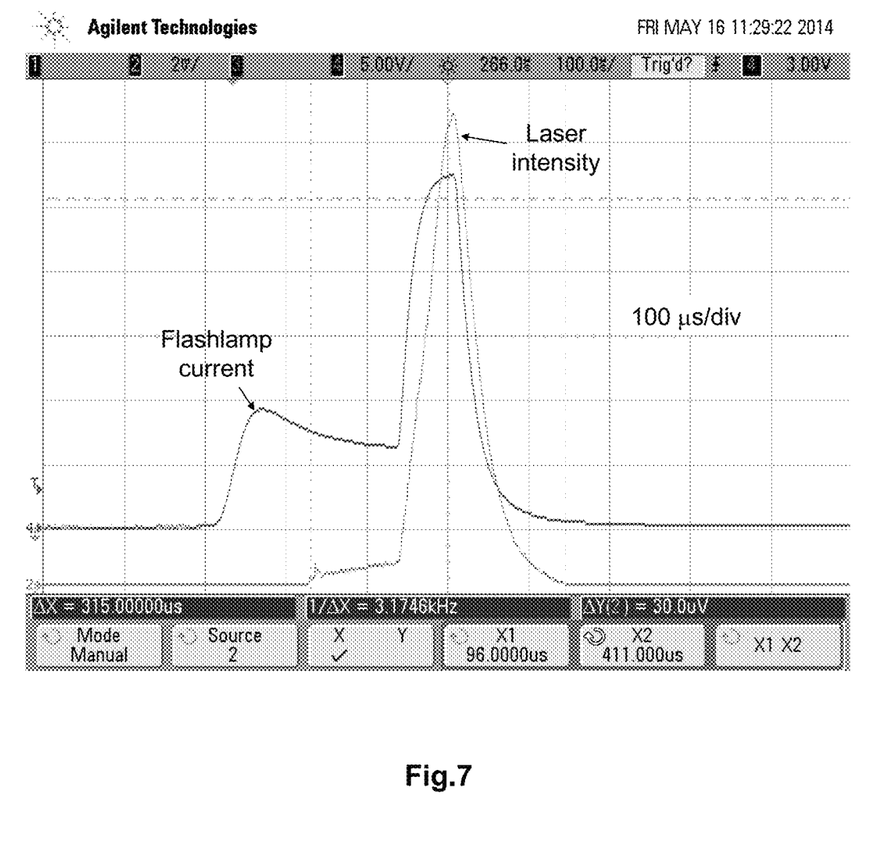
FIG. 7 an example of a PWM flash lamp current pulse and the resulting inventive laser intensity pulse.

There is a deliberate difference between the ideal example of the right-shifted pulse shown in FIG. 4b and the pulse of the preferred embodiment shown in FIG. 5. FIG. 4b depicts the ideal right-shifted pulse from the viewpoint of the proposed use of the inventive laser system. As also seen in FIG. 7, the temporal shape of the laser pulse intensity is directly connected to the shape of the flash lamp current. In the example shown in FIG. 4b, the output laser pulse which is a result of a pumping current pulse (not shown in the Figure) starts very slowly, forming a left tail at the beginning. To obtain a laser pulse with such a smooth ramp-up of the intensity, a slowly rising pumping current for the flash lamp would be needed. In fact, the slower the ramp-up of the pumping pulse, the smoother the resulting laser pulse.

Although the laser pulse shape according to FIG. 4b would be most beneficial for the treatments of tissue, it would be very inefficient to generate such laser pulses with a long left tail. This is, since the pumping efficiency is highly dependent on the pumping level. At low pumping current levels the laser operates close to the threshold and is therefore less energy efficient. Therefore, in order to ensure efficient pumping of the laser, the pumping current needs to rise with a certain minimum speed. In particular, the pumping current should reach a certain minimum level which is preferably at least 10% above the threshold pumping current density ($I_{th}$) within a time period which is shorter than $0.50 \times T_p$, and preferably shorter than $0.25 \times T_p$. Here, the threshold pumping current density ($I_{th}$) is the current density where laser operation reaches its threshold when pumped with a constant pump current density $I_{th}$ for a duration $T_p$. It should be appreciated that the overall duration of the pumping current pulse is typically longer than the duration of the resulting output laser pulse $T_p$, since during the initial part of the current pulse the laser is still below threshold.

Additionally, if the pumping means comprises a flash lamp as an optical pump light source so that the pulsed current from the current source flows through the flash lamp, the emitted spectrum of the flash lamp is shifted to longer wavelengths with lower photon energy, if very low pump currents are used. However, a flash lamp spectrum which is shifted to lower energies is less efficient for pumping the active material of the laser. This is another reason why the pumping current has to reach a certain minimum level within a certain time period. As a result, there is a trade-off for the speed with which the pump current should rise; on the one hand, the pump current should rise slowly, in order to get a laser pulse with a long left tail. On the other hand, the pump current should increase with a minimum speed so that the laser is pumped in an efficient way. In the preferred embodiment according to FIG. 5, this compromise is achieved, since the flash lamp pump current rises rather quickly to a level that achieves efficient pumping of the laser and is held at that current during the first part of the pulse. A steep rise in the flash lamp current at the beginning of the second part of the pulse assures that the laser intensity/laser power rises and that the laser pulse becomes right-shifted. Finally, in order to achieve a steep decline of the pulse intensity/laser power at the end of the right-shifted laser pulse, the pump current is terminated in the fastest possible manner. Here, the fundamental limitation is related to the plasma lifetime of the flash lamp.

Typical flash lamp pump current densities are in the range from 200 to 8000 A/cm$^2$. Our measurements show that the minimal initial flash lamp current density according to one of the preferred embodiments our invention where the output optical spectrum becomes adequate is above 1000 A/cm$^2$. Therefore, the flash lamp pumping current needs to rise with a minimum speed, i.e., reach the minimum level of 1000 A/cm$^2$ within a time period which is shorter than $0.5 \times T_p$ and, preferably, shorter than $0.25 \times T_p$.

In contrast to the prior art pulses shown in FIGS. 2 and 3, the high intensity spiking/high power spiking is absent during the slow ramp up of the inventive PWM pulses shown in FIG. 5.

Referring now to FIG. 7, an example is shown for a PWM generated flash lamp current pulse shape for pumping a solid state medical Er:YAG laser, and the resulting inventive laser intensity pulse.

There are many potential clinical uses of the inventive pulse shape for tissue treatments. Some of the preferred embodiments are described below.

a) Ablation

In one type of treatments, lasers are used for removal of hard and soft body tissues such as dental enamel, dentine, bone material, skin and mucosa. The laser absorption in the ablated tissue leads to local heating with sudden evaporation that causes material removal. Depending on the laser intensity, two distinct ablation regimes can be encountered during laser ablation. At low intensities, the speed of ablation is lower than the speed at which the laser generated heat diffuses away from the ablated surface area deeper into the tissue. In this regime, the thermally influenced layer of tissue that is not ablated by the end of the laser pulse is relatively thick. For most medical procedures this "hot" regime is not desirable since it may result in thermal tissue necrosis. At high laser intensities, however, the ablation front progresses into the tissue faster than heat diffusion. In this, "cold" regime, most of the preheated tissue is eventually ablated by the end of the pulse, and the amount of remaining deposited heat within the tissue is low.

Assuming a constant intensity during the overall pulse duration ($T_p$), and also across the beam spot (S), the minimal intensity $I_c$ that is required for a pulse to ablate in the cold regime, is determined by the amplitude at which the ablation front just catches the diffusion wave at the end of the pulse. The corresponding minimal cumulative pulse energy ($E_c$) that is required to obtain cold ablation is therefore $E_c = I_c \times T_p \times S$. In order to evaluate how the skewness of a pulse influences the thermal effects of ablation, we consider a left- and a right-shifted pulse, both with $E(T_p) = E_c$. For the left-shifted pulse, the ablation during the first half of the pulse is cold. This is because during the first half of the left-shifted pulse with $E(T_p)=E_c$, the average intensity is larger than $I_c$. Therefore, at $t=T_p/2$, there is no thermal layer remaining. However, during the second half of the pulse, the ablation is hot because the average intensity during the second half of the pulse is lower than $I_c$. As a result, ablation with the left-shifted pulse is hot since it produces a thermally affected tissue layer.

In contrast, the inventive right-shifted pulses show different ablation characteristics. The ablation during the first half of the right-shifted pulse is hot, with a thermal layer remaining at $t=T_p/2$. However, the ablation during the last half of the right-shifted pulse is cold, and the preheated tissue remaining from the first half of the pulse is eventually ablated by the end of the pulse. Thus, heat which is deposited into the tissue during first half of the pulse is beneficially used up by the second half of the pulse. Therefore, overall, the ablation with the right-shifted pulse is cold, since there is no thermally affected tissue layer left at the end of the pulse.

In conclusion, for the same pulse duration ($T_p$) and cumulative energy ($E(T_p)$), using a left-shifted pulse shape is not desirable from the viewpoint of heat deposition as it will result in "hotter" ablation in comparison to a right-shifted pulse. In addition, when the initial high intensity spiking and undesirable effects for the laser-water interaction of the left-shifted pulses are taken into consideration, the conclusion is that it is more advantageous for ablative treatments to use right-shifted laser pulses, particularly when water spray cooling is applied during ablation.

b) Treatment of Vascular Lesions

Laser therapy of vascular lesions is based on selective coagulation of undesirable vascular structures using pulsed lasers. However, since the laser light has to pass though epidermis in order to reach the vasculature, non-specific absorption of the laser light by melanin induces epidermal heating, which may lead to blistering, depigmentation, or scarring of treated skin. Absorption in melanin thus limits the intensity of laser light that can be safely applied in laser treatment. What is desired therefore is a means to selectively increase the absorption of the laser light in vasculature during therapy without significantly affecting the temperature of epidermis. This can be accomplished by pre-irradiating the skin with a low intensity laser light, thus inducing slow bulk dermal heating without overheating the epidermis. Namely, it is well known that heating of blood transforms oxy-hemoglobin to met-hemoglobin, which changes the absorption characteristics of blood. For example, laser heating significantly increases light absorption in blood at 1.064 μm which is one of the wavelengths of Nd:YAG and diode lasers used for vascular treatments. It is important to note that pre-heating is preferentially made slowly, with a low intensity laser pulse. Otherwise the high absorbing epidermis could overheat as it would not have sufficient time to cool down by heat diffusion deeper into the dermis.

The inventive right-shifted pulse is particularly suited for carrying out the above described temperature-enhanced vascular therapy. The initial low intensity segment of the pulse slowly preheats bulk dermis and increases absorption of the laser light in blood without overheating the epidermis. The final high intensity part of the pulse then effectively coagulates the treated vasculature. Because of the absorption enhancement during the initial low intensity pre-heating, the total therapeutic cumulative pulse energy can be reduced, increasing the safety margin in laser vascular treatments. One preferred embodiment involves the use of Nd:YAG (1.064 μm) laser configured to generate inventive right-shifted pulses with an overall pulse duration ($T_p$) in a range from 0.02 millisecond inclusive to 500 milliseconds inclusive, the pulse duration depending on the size and the corresponding thermal relaxation time of the vessel being treated.

c) Hair Removal

Laser hair removal has received wide clinical acceptance in both medical and aesthetics settings. Commercial laser systems differ in wavelength, pulse duration and fluence; all of which have an effect on the outcome of the treatment. The choice of wavelength for hair removal is dictated by the need for good absorption of the laser energy in the hair follicle, which lies deep in the skin. Typically, however, the wavelengths that are highly absorbed in skin imperfections are also highly absorbed by non-target structures, for example, melanosomes or hemoglobin. Consequently, these wavelengths do not reach deeper lying hair follicles, and can result in excessive damage to epidermis and other skin structures. For this reason, very often a laser wavelength is selected that penetrates more deeply into the tissue. One of the challenges when performing laser hair removal with such wavelengths is therefore the relatively low absorption of laser light in the treated hair. In order to increase absorption in hair at the treatment laser wavelength, early hair removal techniques were based on infiltrating black carbon into hair ducts. However, it was shown that carbonization of the hair occurs also as a result of heating, which can be achieved by irradiating the hair with laser light. This suggests that the absorption of laser light in hair can be enhanced by the hair removal laser light itself. By delivering laser energy with inventive right-shifted pulses, the absorption of laser light in hair is progressively increased during the pulse, from initial low intensity to the intensity peak towards the end of the pulse, leading to avalanche in the hair temperature and carbonization of hair, followed by higher absorption at the end of the laser pulse and resulting destruction of the hair. The described method results in effective hair removal at lower cumulative pulse fluences than are typically used in hair removal and consequently, less pain and thermal damage to the patient's skin In some of the preferred embodiments an Nd:YAG (1.064 μm) laser, an alexandrite laser (0.755 μm) or a ruby laser (0.964 μm), configured to generate inventive right-shifted pulses is used, whereas the overall pulse duration ($T_p$) is in a range from 0.02 millisecond inclusive to 500 milliseconds inclusive, the pulse duration depending on the size and the corresponding thermal relaxation time of the treated hair.

In conclusion, according to the invention, the temporal development of laser power during the limited duration ($T_p$) of a laser pulse (temporal laser pulse shape) is right-shifted, characterized by the amount of cumulative energy that is delivered during the first half of the pulse (i.e., from the beginning of the pulse at $t=0$ until and including $t=T_p/2$), representing less than 50%, preferably less than 40%, and expediently not more than 25% of the cumulative energy ($E(T_p)$) of the pulse.

The pulse length $T_p$ is defined as the temporal distance between the beginning of the pulse, and the time when at least 99% of the total cumulative energy has been delivered.

In one of the preferred embodiments, at least 50% of the cumulative energy is delivered within the last $\frac{1}{4}^{th}$ of the pulse.

In yet another of the preferred embodiments, the full width half maximum of an intensity temporal pulse shape is on the time axis located closer to the end than to the beginning of the pulse, whereas the intensity temporal shape has been smoothed out to get rid of any fast irregular oscillations. Smoothing out of a single pulse shape is carried out as follows. The pulse power is first integrated in order to obtain a cumulative energy curve. In the second step, the cumulated energy curve is smoothened out, for example, by removing Fourier components with frequencies f, higher than $f=1000/T_p$; and in the final step, the smoothed out power curve is obtained by taking the derivative of the smoothed out cumulative energy curve. Alternatively, the smoothed pulse power can be obtained by averaging at least 16 individual laser pulses.

In the following preferred embodiments are described to facilitate a deeper understanding of the invention:

Embodiment 1

Laser system for medical treatment, comprising:
a pump,
wherein the laser system is adapted to be operated in pulsed operation so that at least one laser pulse of a temporally limited pulse duration ($T_p$) is generated,
wherein said laser pulse irradiates some part of the human or animal body so that a two-dimensional laser spot S is located on the top layer of the irradiated part of the human or animal body; and
wherein the pump power of the pump is modulated in such a way that the cumulative energy $E_S(T_p/2)$ which is delivered by said laser pulse to said laser spot S during the first half of the pulse duration is less than 45% of the energy $E_S(T_p)$ which is delivered by said laser pulse to said laser spot S during the entire pulse duration $T_p$.

Embodiment 2

Laser system according to embodiment 1, wherein the cumulative energy $E_S(T_p/2)$ which is delivered by said laser pulse to said laser spot S during the first half of the pulse duration is less than 35% of the energy $E_S(T_p)$ which is delivered by said laser pulse to said laser spot S during the entire pulse duration $T_p$.

Embodiment 3

Laser system according to embodiment 1, wherein the cumulative energy $E_S(T_p/2)$ which is delivered by said laser pulse to said laser spot S during the first half of the pulse duration is less than 25% of the energy $E_S(T_p)$ which is delivered by said laser pulse to said laser spot S during the entire pulse duration $T_p$.

Embodiment 4

Laser system according to any of the preceding embodiments 1 to 3, wherein the cumulative energy which is delivered by said laser pulse to said laser spot during the last quarter of the pulse, i.e. during the time span $\frac{3}{4}T_p < t < T_p$, is more than 50% of the energy which is delivered by said laser pulse to said laser spot during the entire pulse duration.

Embodiment 5

Laser system according to any of the preceding embodiments 1 to 4, wherein, for times T in the interval [$T_p/20$, $T_p/2$], it holds for the cumulative pulse energy $E_S(T)$ which is delivered by said laser pulse to said laser spot S until time T $$E_S(T) < 0.5 \cdot T \cdot \frac{E_S(T_p)}{T_p},$$

wherein $E_S(T_p)$ is the energy which is delivered by said laser pulse to said laser spot during the entire pulse duration $T_p$, wherein the laser pulse starts at t=0.

Embodiment 6

Laser system according to any of the preceding embodiments 1 to 5, wherein, for all times T in the interval [$T_p/20$, $T_p/4$], it holds $$E_S(T) < 0.25 \cdot T \cdot \frac{E_S(T_p)}{T_p}.$$

Embodiment 7

Laser system according to embodiment 6, wherein, for all times T in the interval [$T_p/20$, $T_p/2$], it holds $$E_S(T) < 0.25 \cdot T \cdot \frac{E_S(T_p)}{T_p}.$$

Embodiment 8

Laser system according to any of the preceding embodiments, wherein the pulse duration ($T_p$) is in the range between 0.020 milliseconds inclusive and 500 milliseconds inclusive.

Embodiment 9

Laser system according to any of the preceding embodiments, wherein said laser pulse comprises a plurality of micro-pulses, wherein in between two micro-pulses of the laser pulse there is a temporal region of the pulse where the pulse intensity is smaller than $\frac{1}{10}^{th}$ of the maximal pulse intensity in the neighboring two micro-pulses.

Embodiment 10

Laser system according to embodiment 9, wherein the time duration of a temporal region of the pulse where the pulse intensity is smaller than $\frac{1}{10}^{th}$ of the maximal pulse intensity in the neighboring two micro-pulses lies between 0.1 microseconds and 2 milliseconds.

Embodiment 11

Laser system according to any of the preceding embodiments, wherein the laser system further comprises a unit which delivers a water spray (i.e., a water sprayer 150, FIG. 1) used for cooling and hydrating the irradiated part of the human or animal body.

Embodiment 12

Laser system according to any of the preceding embodiments, wherein the laser system comprises a PWM power supply.

Embodiment 13

Laser system according to any of the preceding embodiments, wherein the pumping current which is input into the pump reaches a level which is at least 10% above the threshold pumping current density ($I_{thresh}$) within a time period that is shorter than $0.50 \times T_p$, wherein the threshold pumping current density ($I_{thresh}$) is the minimal pumping current density so that the laser reaches the lasing threshold when pumped with a constant pumping current density.

Embodiment 14

Laser system according to any of the preceding embodiments 1 to 13, wherein the laser system is used for one of the following medical treatments: ablation of tissue; treatment of vascular lesions; and hair removal.

What is claimed is:

1. A Laser system for medical treatment, comprising:
a pump,
   wherein the laser system is adapted to be operated in pulsed operation so that at least one laser pulse of a temporally limited pulse duration ($T_p$) is generated,
   wherein said laser pulse irradiates some part of a human or animal body so that a two-dimensional laser spot (S) is located on a top layer of an irradiated part of the human or animal body; and
   wherein a pump power of the pump is modulated in such a way that a cumulative energy ($E_S(T_p/2)$) which is delivered by said laser pulse to said laser spot (S) during a first half of the temporally limited pulse duration is less than 45% of an energy ($E_S(T_p)$) which is delivered by said laser pulse to said laser spot (S) during an entire of the temporally limited pulse duration ($T_p$),
   wherein said laser pulse comprises a plurality of micro-pulses, wherein in between two micro-pulses of the laser pulse there is a temporal region of the laser pulse where a pulse intensity is smaller than $1/10^{th}$ of a maximal pulse intensity for the two micro-pulses, and
   wherein a time duration of the temporal region of the laser pulse where the pulse intensity is smaller than $1/10^{th}$ of the maximal pulse intensity for the neighboring two micro-pulses lies between 0.1 microseconds and 2 milliseconds.

2. The Laser system according to claim 1, wherein the cumulative energy ($E_S(T_p/2)$) which is delivered by said laser pulse to said laser spot (S) during the first half of the pulse duration is less than 35% of the energy ($E_S(T_p)$) which is delivered by said laser pulse to said laser spot (S) during the entire temporally limited pulse duration ($T_p$).

3. The Laser system according to claim 2, wherein the cumulative energy ($E_S(T_p/2)$) which is delivered by said laser pulse to said laser spot (S) during the first half of the pulse duration is less than 25% of the energy ($E_S(T_p)$) which is delivered by said laser pulse to said laser spot (S) during the entire temporally limited pulse duration ($T_p$).

4. The Laser system according to claim 1, wherein the cumulative energy which is delivered by said laser pulse to said laser spot during the last quarter of the pulse, i.e. during the time span $3/4\, T_p < t < T_p$, is more than 50% of the energy which is delivered by said laser pulse to said laser spot during the entire pulse duration.

5. The Laser system according to claim 1, wherein, for times (T) in the interval $[T_p/20, T_p/2]$, it holds for the cumulative pulse energy ($E_S(T)$) which is delivered by said laser pulse to said laser spot (S), until time (T)

$$E_S(T) < 0.5 \cdot T \cdot \frac{E_S(T_p)}{T_p},$$

wherein $E_S(T_P)$ is the energy which is delivered by said laser pulse to said laser spot during the entire temporally limited pulse duration ($T_p$), wherein the laser pulse starts at t=0.

6. The Laser system according to claim 1, wherein, for all times (T) in an interval $[T_p/20, T_p/4]$, it holds $$E_S(T) < 0.25 \cdot T \cdot \frac{E_S(T_p)}{T_p}.$$

7. The Laser system according to claim 6, wherein, for all times (T) in an interval $[T_p/20, T_p/2]$, it holds $$E_S(T) < 0.25 \cdot T \cdot \frac{E_S(T_p)}{T_p}.$$

8. The Laser system according to claim 1, wherein the temporally limited pulse duration ($T_p$) is in a range between 0.020 milliseconds inclusive and 500 milliseconds inclusive.

9. The Laser system according to claim 1, wherein the laser system further comprises water sprayer.

10. The Laser system according to claim 1, wherein the laser system comprises a Pulse Width Modulation (PWM) power supply.

11. The Laser system according to claim 1, wherein the pumping current which is input into the pump reaches a level which is at least 10% above the threshold pumping current density ($I_{thresh}$) within a time period that is shorter than $0.50 \times T_p$, wherein the threshold pumping current density ($I_{thresh}$) is the minimal pumping current density so that the laser reaches the lasing threshold when pumped with a constant pumping current density.

12. The Laser system according to claim 1, wherein the laser system is used for one of the following medical treatments: ablation of tissue; treatment of vascular lesions; and hair removal.

* * * * *